United States Patent [19]

Kirsch et al.

[11] 4,132,650

[45] Jan. 2, 1979

[54] FUSED FIBER BLOOD FILTER

[75] Inventors: Ulrich Kirsch, Melsungen; Manfred Krull, Heiligkreuzsteinach, both of Fed. Rep. of Germany

[73] Assignees: B. Braun Melsungen Aktiengesellschaft, Melsungen; Carl Freudenberg, Kommanditgesellschaft, Weinheim, both of Fed. Rep. of Germany

[21] Appl. No.: 522,308

[22] Filed: Nov. 8, 1974

[30] Foreign Application Priority Data

Nov. 12, 1973 [DE] Fed. Rep. of Germany ....... 2356353

[51] Int. Cl.$^2$ ............................................ B01D 25/06
[52] U.S. Cl. .................................. 210/491; 210/505; 210/508; 210/DIG. 23; 428/253
[58] Field of Search ............... 210/489, 490, 491, 496, 210/503, 504, 505, 508, 509, 510, DIG. 23; 55/523, 528, 524, 482, 485, 486; 428/253

[56] References Cited

U.S. PATENT DOCUMENTS

| | | | |
|---|---|---|---|
| 1,411,975 | 4/1922 | Matson | 210/491 |
| 2,355,822 | 8/1944 | Rugeley | 210/490 |
| 2,676,128 | 4/1954 | Piccard | 55/524 |
| 3,558,412 | 1/1971 | Kurz | 428/253 |
| 3,577,707 | 5/1971 | White | 55/524 |
| 3,613,639 | 10/1971 | Lee | 55/524 |
| 3,622,446 | 11/1971 | Burnham | 55/524 |
| 3,632,415 | 1/1972 | Franklin | 210/509 |
| 3,731,815 | 5/1973 | Collingwood et al. | 210/496 |
| 3,762,564 | 10/1973 | Weedon et al. | 210/505 |

*Primary Examiner*—Charles N. Hart
*Assistant Examiner*—Ernest G. Therkorn
*Attorney, Agent, or Firm*—Curtis, Morris & Safford

[57] ABSTRACT

A filter element that is particularly suitable for filtration of blood is made by compacting a mixture of fibers that is non-injurious to blood and one component of which has a lower softening temperature than the other component or components at a temperature sufficient to soften said fiber component and thereby bind the various fiber components together to form a stable and substantially uniform filter element.

8 Claims, No Drawings

FUSED FIBER BLOOD FILTER

The present invention relates to a filter for filtering blood, which comprises a filter element consisting of a compacted body of fibers that are non-injurious to blood, and to a method for making such filter elements.

When blood for transfusions has been withdrawn from the donor, it is generally mixed with a solution which inactivates the coagulation system of the blood by binding the calcium ions and thus prevents the withdrawn blood from coagulating until it is transfused. The natural process of blood from coagulation can most easily be compared with a gelling process, i.e. the total quantity of blood forms one single clot. This gelling process is prevented by the addition of stabilizing solutions. Such solutions do not, however, prevent formation of small aggregates which mainly consist of coagulating blood-plates, the thrombocytes, and of white blood corpuscles, the leucocytes. In addition, the red blood corpuscles participate in the coagulation by being stuck to or incorporated into the aggregate. These fine aggregates are of no use to the receiver of the blood, but are harmful in that fine capillaries of the lungs are temporarily or even permanently obstructed by these coagula resulting in a lung disease which may be fatal.

The necessity of subjecting whole blood to filtration before its transfusion is generally known in medicine. Every system for the transfusion of blood is therefore provided with a filtering screen, as stipulated in th pharmacopeia of certain countries.

The efficiency of net-like or screen-like filters is limited because of the fact that the filter is rapidly obstructed when the mesh size is too fine and, as a result, it is not possible to filter a sufficient quantity of blood. Conventional net-like or screen-like blood fitlers have a mesh size of 200 microns, or less frequently of 100 microns. Of late, mesh sizes of 40 microns have also been used.

These filters retain fairly large aggregates. This is undoubtedly advantageous for the patient because it avoids obstruction, by larger blood aggregates, of the minor arteries of the lungs leading to a relatively large number of lung capillaries which could be cut off from circulation by a single coagulum of fairly large size. However, aggregates having dimensions large enough to be retained by these net-like or screen-like filters occur relatively rarely, as compared to the frequently occurring, considerably smaller aggregates of a dimension in the range of from 10 to 25 microns. Moreover, these smaller aggregates have a plastic consistency and may therefore pass through even those pores which seem to be too narrow. Furthermore, it should be mentioned that also the larger aggregates can pass through the filter since they can be divided easily, so that the smaller but nevertheless still dangerous fragments emerge behind such filters.

In 1961, Swank proposed to filter blood with filters consisting of fibrous materials in order to remove the microaggregates (The New England Journal of Medicine, vol. 265, pages 728–733 (1961)). He was able to test the efficiency of such filters by means of an experimental procedure which he had developed. According to this experimental procedure, the pressure head developed upstream of a test filter is determined as a dependent variable. When a test filter of standardized surface area (a diameter of 25 mm.) and constant pore size is used and blood is led through at a standardized constant speed, an upstream pressure head is built up at the leading side of the filter which at first depends only on the viscosity of the blood, but is increased within a short time because of the fact that the stream bed is narrowed by blood aggregates obstructing the filter meshes.

In the method according to Swank, a metal screen having square openings of an edge length of 20 microns is used. This showed that fibrous materials may be advantageously used for the removal of aggregates from blood. As a result, blood filters were constructed, as are described, e.g., in German Auslegeschrift No. 1,928,052 and in German Auslegeschrift No. 2,116,497.

Such filters have structural and functional deficiencies, and their suitability for the clinical application to the patient is therefore uncertain. Pressing fiber masses into a casing necessarily entails certain irregularities in the packing density. Especially at the border of the packing, a gap is formed between the fiber plug and the smooth wall of the casing. The blood led through the filter will naturally prefer the path of least resistance, i.e. it will pass the filter at those places where the filtration effect is least or even completely missing. Another disadvantage in the use of fibrous materials heretofore resides in the fact that the fiber accumulation must be secured at the leading side or the trailing side by means of supports, for example screens. Another disadvantage, which is especially serious for the patient, is the fact that it is possible at any time that individual fiber fragments or short fiber ends may be carried along the with blood stream through succeeding supporting means and thus get into the patient's lungs where they may cause the formation of a foreign body granuloma. This formation of a foreign body granuloma caused by fibrous or other foreign bodies which have been introduced via the venous system is a known danger.

Surprisingly, the examination of the findings published by Swank showed that the results of the filtration of blood through fibrous materials depend not only on the thickness and compression of the fibrous materials, but also on the mesh size of the filter used in the subsequent test. When using a filter having a mesh size lower than that of the screen used by Swank, for example of 14 ± 3 microns instead of 20 microns as indicated by Swank, it was found that blood which seemed to be free from aggregates according to the method by Swank (test filter having a mesh size of 20 microns) contained a large number of aggregates capable of obstructing a test of 14 ± 3 microns. Since the disk-shaped erythrocytes have diameters of at most about 7.5 microns, particles having a diameter of more than 10 microns are undesirable as blood components for blood transfusions because they may be decaying leucocytes or aggregates.

The known methods of blood filtration were therefore examined with a finer test filter. In this experimental arrangement a so-called millipore-filter having a pore size of 14 ± 3 microns was used which covers a circular surface having a diameter of 25 mm. The blood to be tested is pressed under constant pressure through this filter and, in modification of the dependent variables given by Swank, the volume is determined which can get through the filter until it is completely obstructed.

Typical values of this method are, for example, the following: Under a pressure of 200 mm/Hg, about 50 ml of ACD-blood freshly taken from the donor may pass the 25 mm. diameter filter before it is completely obstructed. The formation of aggregates in this stored blood becomes evident by the fact that the quantity of blood sufficient to obstruct the test filter becomes smaller and smaller upon prolonged storage. For example, the quantity sufficient to obstruct the test filter completely is 20 ml after 24 hours of storage, 12 ml after 48 hours, 8 ml after 72 hours and 6 ml after ten days. However, even a test filter having a pore size of 14 ± 3 microns cannot filter the blood completely. Thus, it is not possible to pass an unlimited quantity of the blood which has previously been prefiltered by means of the test filter through the said filter; a three-to-ten fold quantity will obstruct a succeeding second test filter of the same mesh size.

The method described was used to test conventional screen filters having a mesh size of 40 microns, as well as filters containing fibers as filter material. It was found that conventional screen filters having a mesh size of 40 microns are efficient only if the blood contains no small aggregates of less than approximately 20 microns, but mainly very large aggregates. Fiber packings are also inefficient if there are no large aggregates in the blood which may be caught in the relatively loose fiber tangle. This was obvious from the results achieved by Solis, R. T. and M. B. Gibbs (Filtration of the Microaggregates in Stored Blood, "Transfusion," 12, 245–250, 1972).

They found that approximately 80% of the aggregates present in unfiltered stored blood have a diameter of less than 20 microns. However, such aggregates cannot be controlled by Swank's original method, which is the basis for postulating the efficiency of fiber filters. The examination of fiber materials showed that, according to the testing method using a test filter of 14 ± 3 microns, the efficiency of these fiber materials is reliable only if they have been compressed to about 0.7 g/cm$^3$. This is approximately the maximal rate of compression which can be obtained without changing the fiber geometry. In contradistinction thereto, German Auslegeschrift No. 2,116,497 indicates a density of 0.2 g/cm$^3$ as being most favorable.

Another disadvantage of the known fiber filters, besides poor efficiency, is the insufficient tightening of the fiber plug at the edge. In addition, special means for supporting the fiber plug are necessary. Finally, the patient is exposed to danger by sporadic, but altogether too numerous fiber particles in the filtrate.

It is the object of the present invention to manufacture fiber filters suitable for the filtration of blood by which the disadvantages described above may be largely avoided, especially with regard to the danger of fiber fragments being carried along with the blood stream.

This object has been achieved in accordance with the invention by compacting a mixture of fibers that is non-injurious to blood and is composed of fiber components having differently high softening ranges, or a mixture of fibers, at least one component of which may be brought to softening by heating, into a uniform layer, for example between two heated metal surfaces or rollers, while heating to a temperature which corresponds to the softening range of the fiber portion which has the lowest softening point. The metal surfaces or rollers used are advantageously highly polished metal rollers. Compression may also be effected by means of multilayer pressing under usual pressures.

As a result of the softening of a portion of the fibers, the compressed fiber mixture is permanently fixed in this compressed form. The individual fibers in the fiber packing which have no softening range or a higher one are bound to one another by the adhesion of the softened and thus adhering fiber portions so sufficiently and tightly that during the filtration of blood, no fiber particles are carried along with the blood stream through the fibrous filter material.

The fiber mixtures are advantageously compressed and thermofixed in such a manner that solid filter plates are obtained having a density of from about 0.2 g/cm$^3$ to about 3.5 g/cm$^3$, preferably of about 0.7 g/cm$^3$, and a thickness of from about 0.1 mm to about 30 mm, preferably from about 1.5 mm to 3 mm.

For the fibrous filter material used in accordance with the invention, there may be employed all fibers that are non-injurious to blood. The mixture should contain, in a quantity sufficient to bind the other fibers, at least one fiber which has a softening range lower than that of the other fiber component or, optionally, of the several other fiber components. Examples of suitable fibers are synthetic fibers of polyesters, polyamides, polyacrylonitrile, polyethylene, polypropylene, polyvinyl chloride, rayon, furthermore wool, cotton, silk, as well as fibers of metals, metal alloys, glass, asbestos, etc.

A suitable fiber mixture is, for example, a mixture of polyester fibers and polyamide fibers at a ratio of about 80% to about 20%, the polyamide fibers having the lower softening range; or a mixture of polyester fibers and polyvinyl chloride fibers at a ratio of about 70% to about 30%, the polyvinyl chloride fibers having the lower softening range. The softening ranges are approximately 110° C. for the polyvinyl chloride fibers, approximately 140° C. for the polypropylene fibers, approximately 160° C. for the polyamide fibers and approximately 180° C. for a polyester fiber of polyethylene terephthalate.

A special embodiment of the invention comprises an additional layer consisting only of fibers having a low softening range, which layer is applied to the fiber mixture to be compacted.

In general, the proportion of fibers having a lower softening range may be less than that of the fibers having no softening range or a higher one.

The fibrous filter plates prepared in accordance with the invention are solid bodies, the structure of which is similar to that of wood fiber boards. A special advantage of the use of the filter elements for the filtration of blood is the fact that they may be inserted into filter casings without supporting means, for example screens.

The wettability of the filter material may be improved by treating it with acids, for example dilute hydrochloric acid.

The invention is further illustrated in the following examples.

EXAMPLE 1

ACD-stabilized whole human blood prefiltered by one of three types of filters after storage as prescribed for eight days was used to determine the efficiency of various fiber filter materials by the method described earlier. After the stored blood had been thoroughly stirred, it was passed through the following filters using a standard blood transfusion device:

A. A standard test filter having a pore size of 14 ± 3 microns;
B. A polyester fleece filter having a thickness of 2.6 mm and compacted to a density of 0.4 g/cm$^3$;
C. A filter plate prepared in accordance with the invention, made of a mixture of 80% polyester fibers and 20% polyamide fibers having different softening temperatures, a density of about 0.7 g/cm³ and a thickness of about 1.5 mm.

Two tests were carried out with each type of filter.

With type A, the test filter itself was obstructed by 5.5 ml and 6.5 ml, respectively, of the stored blood.

With type B, in each test 9 ml each of the blood prefiltered by filter type B obstructed the test filter A.

Blood which had been prefiltered by filter type C obstructed the test filter A in both tests only at a quantity of 14.5 ml each.

These tests show that the number of aggregates which may be caught by a test filter having a pore size of 14 ±3 microns can be reduced to about 70% by the prefiltration with the filter material of type B and to about 40% by prefiltration with the filter plate of type C.

EXAMPLE 2

Stabilized human blood stored for eight days again served as test object. The efficiency of a fiber filter material was tested which had a density of 0.7 g/cm³ and had been prepared in accordance with the present invention from a mixture of polyester fibers (70%) and polyvinyl chloride fibers (30%) by compaction and simultaneous thermofixation. In order to improve the wettability of this fiber filter material, it was rinsed for two hours at room temperature with 6N hydrochloric acid, then washed with demineralized water and dried. A quantity of 5.5 ml of blood was sufficient, as mentioned in Example 1, to obstruct a conventional test filter having a pore size of 14 ± 3 microns. After the blood had been prefiltered through the filter plate of the invention, it was found in two tests that upon subsequent filtration 14 ml and 15 ml, respectively, of the prefiltered blood obstructed the test filter of a pore size of 14 ± 3 microns.

As a result, the number of aggregates which may be caught by the test filter was reduced to approximately 30% by prefiltration of the blood using the fibrous filter plate of the present invention.

We claim:

1. A filter for blood which comprises a body of fibers non-injurious to blood compacted to a uniform density and thickness, said fibers comprising a mixture of fibers having different softening temperatures including at least one fiber component which has the lowest softening temperature of the fibers in the mixture and which is softened by heating at its softening temperature whereby the fibers in said mixtures are permanently bonded together; and characterized in that an additional layer, consisting only of fibers having said lowest softening temperature, is applied to one face of the filter.

2. The filter defined in claim 1, characterized in that the filter material has a density of from about 0.2 g/cm³ to about 3.5 g/cm³ and a thickness of from about 0.1 mm to about 30 mm.

3. The filter defined in claim 1, characterized in that the filter material has a density of about 0.7 g/cm³ and a thickness of from about 1.5 mm to about 3 mm.

4. The filter defined in claim 1, characterized in that the proportion of the fibers having the lowest softening temprature is smaller than the proportion of fibers having a higher softening temperature.

5. The filter defined in claim 4, characterized in that the proportion of fibers having the lowest softening temperature is of the order of about 20-40%.

6. The filter defined in claim 1 in which the fibers are a mixture of polyester and polyamide fibers.

7. The filter defined in claim 6 in which the relative proportion of polyester fibers and polyamide fibers is about 80:20.

8. The filter defined in claim 6 in which the relative proportion of polyester fibers and polyvinyl chloride fibers is about 70:30.

* * * * *